(12) United States Patent
Kalita et al.

(10) Patent No.: US 11,040,191 B2
(45) Date of Patent: Jun. 22, 2021

(54) METHOD OF FORMING A MEDICAL DEVICE COMPRISING GRAPHENE

(71) Applicants: Centre National de la Recherche Scientifique, Paris (FR); UNIVERSITE GRENOBLE ALPES, Saint Martin d'Heres (FR)

(72) Inventors: Dipankar Kalita, Grenoble (FR); Vincent Bouchiat, Biviers (FR); Laetitia Marty, Quaix en Chartreuse (FR); Nedjma Bendiab, Grenoble (FR)

(73) Assignees: Centre National de la Recherche Scientifique, Paris (FR); UNIVERSITE GRENOBLE ALPES, Saint Martin (FR)

(*) Notice: Subject to any disclaimer, the term of this patent is extended or adjusted under 35 U.S.C. 154(b) by 505 days.

(21) Appl. No.: 15/556,984

(22) PCT Filed: Mar. 9, 2016

(86) PCT No.: PCT/EP2016/054964
§ 371 (c)(1),
(2) Date: Sep. 8, 2017

(87) PCT Pub. No.: WO2016/142401
PCT Pub. Date: Sep. 15, 2016

(65) Prior Publication Data
US 2018/0056057 A1    Mar. 1, 2018

(30) Foreign Application Priority Data
Mar. 9, 2015    (EP) ..................................... 15305351

(51) Int. Cl.
*H01R 43/00*    (2006.01)
*H05K 13/00*    (2006.01)
(Continued)

(52) U.S. Cl.
CPC ............ *A61N 1/0468* (2013.01); *A61L 27/08* (2013.01); *A61L 27/34* (2013.01); *A61L 27/50* (2013.01);
(Continued)

(58) Field of Classification Search
CPC .. A61N 1/0551; A61N 1/0492; A61N 1/0468; A61F 9/0017; A61L 27/08;
(Continued)

(56) References Cited

U.S. PATENT DOCUMENTS 7,945,302 B2    5/2011    McAdams
9,567,223 B2*   2/2017    Song .................... C01B 32/194
(Continued)

FOREIGN PATENT DOCUMENTS

CN    101048055    10/2007
CN    102920452 A    2/2013
(Continued)

OTHER PUBLICATIONS

Office Action received for European Patent Application No. 15305351.7, dated Sep. 21, 2015, 12 pages.
(Continued)

*Primary Examiner* — Paul D Kim
(74) *Attorney, Agent, or Firm* — Kaplan Breyer Schwarz, LLP

(57) ABSTRACT

The invention concerns a method of forming a medical device, the method comprising: forming a graphene film (100) over a substrate (204); depositing, by gas phase deposition, a polymer material covering a surface of the graphene film (100); and removing the substrate (204) from the graphene film (100), wherein the polymer material forms a support (102) for the graphene film (100).

12 Claims, 4 Drawing Sheets

(51) Int. Cl.

| | |
|---|---|
| A61N 1/04 | (2006.01) |
| A61L 27/08 | (2006.01) |
| A61L 27/34 | (2006.01) |
| A61L 27/50 | (2006.01) |
| A61L 31/02 | (2006.01) |
| A61L 31/10 | (2006.01) |
| A61L 31/14 | (2006.01) |
| A61N 1/05 | (2006.01) |
| C01B 32/194 | (2017.01) |
| A61F 9/00 | (2006.01) |

(52) U.S. Cl.
CPC ............ *A61L 31/024* (2013.01); *A61L 31/10* (2013.01); *A61L 31/14* (2013.01); *A61N 1/0492* (2013.01); *A61N 1/05* (2013.01); *C01B 32/194* (2017.08); *A61F 9/00* (2013.01); *A61F 9/0017* (2013.01); *A61N 1/0551* (2013.01)

(58) Field of Classification Search
CPC ........ A61L 27/34; A61L 27/50; A61L 31/024; A61L 31/10; A61L 31/14; C01B 32/194; C08L 65/04
See application file for complete search history.

(56) References Cited

U.S. PATENT DOCUMENTS

| | | | | |
|---|---|---|---|---|
| 2012/0282419 | A1* | 11/2012 | Ahn .................. | B82Y 30/00 428/34.8 |
| 2013/0090542 | A1 | 4/2013 | Kipke et al. | |
| 2013/0130037 | A1 | 5/2013 | Bol et al. | |
| 2013/0285970 | A1 | 10/2013 | Ahn et al. | |
| 2014/0010744 | A1 | 1/2014 | Ruona et al. | |
| 2014/0145139 | A1 | 5/2014 | Huang et al. | |
| 2014/0326700 | A1 | 11/2014 | Bouchiat et al. | |
| 2014/0336597 | A1 | 11/2014 | Coulthard et al. | |
| 2015/0098891 | A1 | 4/2015 | Song et al. | |
| 2015/0343202 | A1 | 12/2015 | Picaud et al. | |
| 2016/0169754 | A1 | 6/2016 | Kowalewski et al. | |
| 2017/0057827 | A1* | 3/2017 | Sultana ............... | H01L 31/1884 |
| 2018/0057361 | A1 | 3/2018 | Kalita et al. | |

FOREIGN PATENT DOCUMENTS

| | | |
|---|---|---|
| CN | 102925859 | 2/2013 |
| CN | 104000624 A | 8/2014 |
| EP | 2747158 A1 | 6/2014 |
| EP | 2778757 A1 | 9/2014 |
| JP | 2011051801 A * | 3/2011 |
| KR | 10-2014-0015927 A | 2/2014 |
| TW | M487718 U | 10/2014 |
| WO | 2013116675 A1 | 8/2013 |
| WO | 2014/145139 | 9/2014 |
| WO | 2015020610 A1 | 2/2015 |

OTHER PUBLICATIONS

Non-Final Rejection received for U.S. Appl. No. 15/557,039, dated Jul. 27, 2018, 15 pages.
Jung et al., KR 10-2014-0015927,Translation (Year: 2014).
Jiyoung Chang et al., "Facile electron-beam lithography technique for irregular and fragile substrates", doi: http://dx.doi.org/10.1063/1.4900505, "Applied Physics Letters", dated Oct. 1, 2014, vol. 105, No. 17.
Jian Zhang et al., "Electron Beam Lithography on Irregular Surfaces Using an Evaporated Resist", DOI: 10.1021/nn4064659, "ACS NANO", dated Mar. 26, 2014, pp. 3483-3489, vol. 8, No. 4, Publisher: American Chemical Society, Published in: CA.
Huan Du et al., "A Virtual Keyboard Based on True-3D Optical Ranging", Published in: CH.

Authorized Officer: Follens, Lana, "International Search Report and Written Opinion" issued in PCT application No. PCT/EP2016/054963, dated Jun. 13, 2016.
Non-Final Rejection received for U.S. Appl. No. 15/557,039, dated Jun. 5, 2019, 17 pages.
Final Rejection received for U.S. Appl. No. 15/557,039, dated Feb. 21, 2019, 16 pages.
Applicant Initiated Interview Summary (PTOL-413) received for U.S. Appl. No. 15/557,039, dated Jun. 5, 2019, 3 pages.
Authorized Officer: Cadamuro, Sergio, "International Search Report and Written Opinion" issued in counterpart PCT application No. PCT/EP2016/054964, dated May 10, 2016.
Patricia Duran Ospina et al., "A Review in Innovation in Ocular Prostheses and Visual Implants: New Biomaterials and Neuro-Implants is the Challenge for the Visual Care", XP055212711, "Journal of Ocular Diseases and Therapeutics", dated Jul. 3, 2014, vol. 2, No. 9-16.
Stan Monstrey et al., "Assessment of burn depth and burn wound healing potential", DOI: http://dx/doi.org/10.1016/j.burns.2008.01.009, "Burns", dated Sep. 1, 2008, pp. 761-769, vol. 34, No. 6, Publisher: Elsevier Inc., Published in: BE.
L. C. Kloth, "Electrical Stinulation for Wound Healing: A Review of Evidence From in Vitro Studies, Animal Experiments, and Clinical Trials", XP055212717, ISSN: 1534-7346, DOI: 10.1177/1534734605275733, "The International Journal of Lower Extremity Wounds", dated Mar. 1, 2005, pp. 23-44, vol. 4, No. 1.
Luther C. Kloth, "Electrical StimulationTechnologies for Wound Healing", DOI: 10.1089/wound.2013.0459, "Advances in Wound Care", dated Mar. 8, 2013, pp. 81-90, vol. 3, No. 2, Publisher: Wound Healing Society.
Wang Y et al., "Electrochemical delamination of CVD-grown graphene film: Toward the recyclable use of copper catalyst", XP002716759, ISSN: 1936-0851, DOI: 10.1021/NN203700W, "ACS NANO", dated Dec. 24, 2011, pp. 9927-9933, vol. 5, No. 12, Publisher: American Chemical Society, Published in: US.
Xianrong Xing et al., "Electrochemical sensor based on molecularly imprinted film at polypyrrole-sulfonated graphene/hyaluronic acid-multiwalled carbon nanotubes modified electrode for determination of tryptamine", XP028353761, ISSN: 0956-5663, DOI: 10.1016/J.BIOS.2011.10.032, "Biosensors and Bioelectronics", dated Oct. 18, 2011, pp. 277-283, vol. 31, No. 1, Publisher: Elsevier BV, Published in: NL.
Zheng Han et al., "Homogeneous Optical and Electronic Properties of Graphene Due to the Suppression of Multilayer Patches During CVD on Copper Foils", dated 2013, DOI: 10.1002/adfm.201301732, "Advanced Functional Materials", pp. 1-7, Publisher: Wiley-VCH Verlag GmbH & Co. KGaA, Weinheim.
G. C. Zografos et al., "Laser Doppler Flowmetry in Evaluation of Cutaneous Wound Blood flow ujsing Various Suturing Techniques", "Ann. Surg.", dated Mar. 1992, pp. 266-268, vol. 215, No. 3, Published in: GB.
Ivan Khrapach et al., "Novel Highley Conductive and Transparent Graphene-Based Conductors", dated 2012, DOI: 10.1002/adma.201200489, "Advanced Materials", pp. 2844-2849, vol. 24, Publisher: Wiley-VCH Verlag GmbH & Co. KGaA, Weinheim.
Applicant Initiated Interview Summary received for U.S. Appl. No. 15/557,039, dated Sep. 11, 2019, 4 pages.
Final Office Action received for U.S. Appl. No. 15/557,039, dated Jan. 8, 2020, 19 pages.
Non-Final Rejection dated Aug. 20, 2020 for U.S. Appl. No. 15/557,039.
English Translation of Office Action issued in Chinese Patent Application No. 201680026580.9 dated Sep. 23, 2020.
Examiner Interview Summary Record (PTOL—413) dated Dec. 22, 2020 for U.S. Appl. No. 15/557,039.
Office Action Appendix dated Dec. 22, 2020 for U.S. Appl. No. 15/557,039.
Tenhaeff et al, Initiated and Oxidative Chemical Vapor Deposition of Polymeric Thin Films: iCVD and oCVD, Apr 18, 2008.
Final Rejection dated Mar. 31, 2021 for U.S. Appl. No. 15/557,039.

* cited by examiner

METHOD OF FORMING A MEDICAL DEVICE COMPRISING GRAPHENE

FIELD

The present disclosure relates to the field of medical devices comprising a conductive layer, and to a method of forming such a medical device.

BACKGROUND

Certain types of medical devices are designed to form a conductive interface with a human or animal body.

For example, certain types of medical patches may comprise a conductive layer held against the skin of a human or animal, and a wire for monitoring an electrical signal on the conductive layer.

As a further example, an ophthalmic element may be positioned on the surface of the eye of a human or animal, and use a conductive layer to shield the eye, or monitor certain properties of the eye.

As yet a further example, a medical implant is a needle-like element that can be inserted into tissue of a human or animal body and comprises an electrically conductive portion allowing electrical signals to be monitored.

Such medical devices should generally comprise a conductive portion with good electrical conductivity, and be capable of maintaining close electrical contact with the skin or tissue of the human or animal body. However, existing devices tend not to be able to sufficiently meet both of these needs simultaneously. Furthermore, such medical devices often use metal layers which are susceptible to oxidization.

SUMMARY

It is an aim of embodiments of the present disclosure to at least partially address one or more needs in the prior art.

According to one aspect, there is provided a method of forming a medical device, the method comprising: forming a graphene film over a substrate; depositing, by gas phase deposition, a polymer material covering a surface of the graphene film; and removing the substrate from the graphene film, wherein the polymer material forms a support for the graphene film.

According to one embodiment, the polymer material comprises a polymer from the n-xylylene family, and for example comprises parylene.

According to one embodiment, removing the substrate from the graphene film is performed by a process of electrochemical delamination.

According to one embodiment, the method is for forming a conductive medical patch, the method further comprising: providing an adhesive band covering the polymer support and suitable for holding the graphene film in contact with a body; and electrically coupling a wire contact to the graphene film.

According to one embodiment, electrically coupling the wire contact to the graphene film comprises, prior to depositing the polymer material, forming the wire contact on the surface of the graphene film, wherein depositing the polymer material comprises coating the wire contact with the polymer material.

According to one embodiment, the method further comprises forming a conductive electrode patch of the conductive medical patch and a current supply circuit, the current supply circuit being adapted to apply a current between the graphene film and the conductive electrode patch, wherein the adhesive band is also suitable for holding the conductive electrode patch in contact with the body.

According to one embodiment, the conductive medical patch is a transparent hydrocolloidal dressing, the graphene film forming an external surface for contact with a wound, and the polymer material being a porous layer positioned between the graphene film and a pad formed of a hydrocolloid.

According to one embodiment, the method is for forming an ophthalmic element, the substrate on which the graphene film is formed having a curved surface having a shape compatible with the surface of an eye.

According to one embodiment, a surface of the substrate on which the graphene film is formed comprises a pattern of first and second materials, the first material and not the second material supporting graphene formation, the method comprising selectively forming said graphene film over said first material and not over said second material.

According to one embodiment, the method is for forming an implant, wherein the substrate on which the graphene film is formed is a mold having an inner surface having the form of the implant, and wherein after the graphene film has been deposited on the inner surface of the mold, the mold is filled by the polymer material to form a polymer core of the implant that supports the graphene film.

According to one embodiment, a portion of the mold is not removed such that it remains in contact with the graphene film and forms an electrode of the implant.

According to one embodiment, the polymer material is deposited over the graphene film in a layer of between 5 and 40 nm in thickness.

According to a further aspect, there is provided a conductive medical patch comprising: a graphene film covered by a layer of a polymer material; and a wire contact electrically coupled to the layer of graphene.

According to one embodiment, the graphene film is capable of contact with a body to which the patch is to be applied, the conductive patch further comprising an adhesive layer for holding the graphene film in contact with the body, wherein the adhesive layer is capable of being removed from the body leaving at least part of the graphene film in place.

According to one embodiment, the polymer material comprises hyaluronic acid.

According to one embodiment, the conductive medical patch is a hydrocolloidal dressing, the graphene film forming an external surface for contact with wound, and the polymer material being a porous layer positioned between the graphene film and a pad formed of a hydrocolloid.

According to a further aspect, there is provided a wound treatment apparatus comprising: the above conductive medical patch for placing over the wound; a further conductive patch; and a voltage application module adapted to apply voltage pulses between the conductive medical patch and the further conductive patch.

According to a further aspect, there is provided an ophthalmic element comprising: a curved plate formed of a graphene film covered by an outer layer of polymer material.

According to a further aspect, there is provided an eye protection device comprising the above ophthalmic element, wherein the graphene film forms a continuous layer across the element.

According to a further aspect, there is provided an implant comprising: a core in the form of a shaft having a pointed end and formed of a polymer material; and a graphene film covering and supported by the polymer core.

BRIEF DESCRIPTION OF THE DRAWINGS

The foregoing and other features and advantages will become apparent from the following detailed description of embodiments, given by way of illustration and not limitation with reference to the accompanying drawings, in which.

For ease of illustration, the various figures are not drawn to scale.

DETAILED DESCRIPTION

Graphene is a substance composed of carbon atoms forming a crystal lattice one atom in thickness. Various applications have been proposed for graphene, including its use in radio-frequency transistors and for forming transparent highly conductive and flexible electrodes, such as for displays. It is of particular benefit in applications where high mobility conductors are desired. Most applications of graphene require a macroscale-sized graphene layer, comprising one or a few layers of carbon atoms, which is transferred onto a substrate of a material selected based on the particular application.

Figure 1:
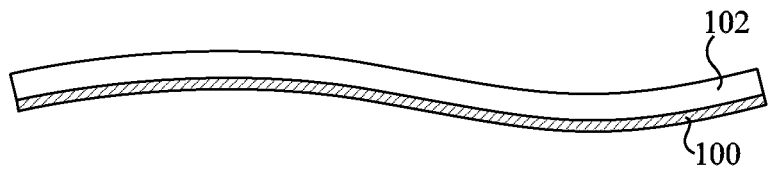
FIG. 1 is a cross-section view of a graphene device according to an example embodiment of the present disclosure.

FIG. 1 is a cross-section view of a graphene device comprising a film 100 of graphene, which is for example just one atom in thickness, or may have a thickness of up to 8 or more atom layers in some embodiments, depending on the application and the desired electrical conductivity. In particular, the graphene film 100 is for example formed of one or a plurality of graphene mono-layers attached together. In some embodiments, the graphene film 100 is doped in order to reduce its surface resistance, for example using P-dopants such as $AuCl_3$ and/or $HNO_3$. Additionally or alternatively, layers of $FeCl_3$ may be intercalated between one or more of the graphene layers to reduce the element resistance. For example, such a technique is described in more detail in the publication entitled "Novel Highly Conductive and Transparent Graphene-Based Conductors", I. Khrapach et al., Advanced Materials 2012, 24, 2844-2849, the contents of which is hereby incorporated by reference.

In plan view (not represented in FIG. 1), the graphene film 100 may have any shape, and for example has a surface area of anywhere between 1 $\mu m^2$ and 200 $cm^2$, depending on application.

The graphene film 100 is covered by a support 102 in the form of a layer of polymer material. The polymer material is for example selected from the family of n-xylylenes, and in one example comprises parylene. Parylene has the advantage of being capable of being stretch by up to 200% before breaking, and is capable of remaining flexible over a relatively wide temperature range. In one example, the polymer material comprises parylene C or parylene N. Both parylene C and parylene N have the advantage of being relative elastic, while parylene N has a slightly lower Young's modulus, and thus a higher elasticity, than parylene C.

As will be described in more detail below, the polymer support 102 has for example been formed by a gas phase deposition technique or by a spin deposition technique. The polymer support 102 for example has a thickness of between 10 nm and a few tens or hundreds of $\mu m$, depending on the application. In some embodiments, the thickness of the polymer support 102 could be as low as 5 nm, and for example in the range 5 to 40 nm.

While in the example of FIG. 1 the polymer support is in the form of a layer having a substantially uniform thickness, as will become apparent from the embodiments described below, the polymer support could take other forms depending on the particular application.

The combination of a graphene film 100 and a polymer support 102 provides a multi-layer that can have relatively high electrical conductance while remaining flexible and strong. Of course, while the multi-layer of FIG. 1 has just two layers—the graphene layer and the parylene layer that form a bi-layer, in alternative embodiments there could be one or more further layers. For example, the graphene layer could be sandwiched by parylene layers on each side, and/or one or more layers of further materials could be formed in contact with the graphene or parylene layer.

Furthermore, the use of a polymer such as parylene leads to a device that is biocompatible, making the device suitable for a variety of medical or physiological applications in which it can for example contact human or animal tissue. The term medical device is used herein to cover any device suitable for close contact with human or animal tissue for the purpose of protection, treatment, diagnosis, or any other purpose.

Figure 2:
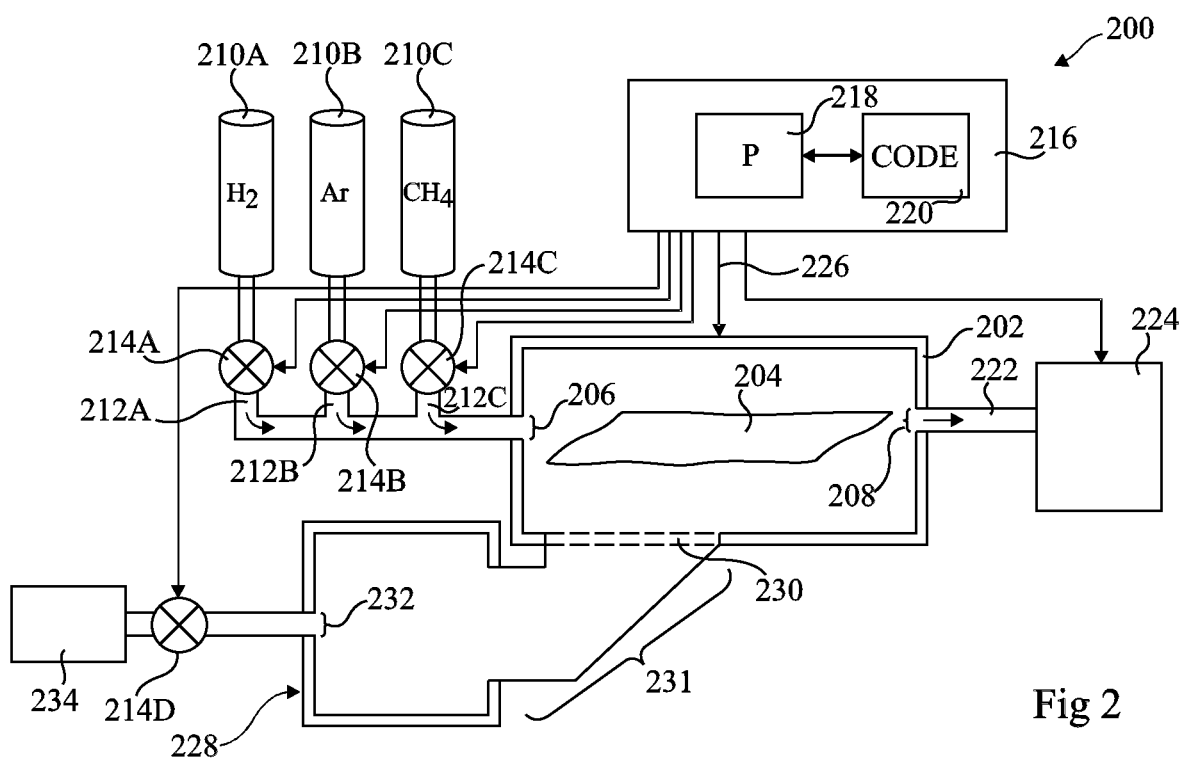
FIG. 2 schematically illustrates an apparatus for forming a graphene device according to an example embodiment of the present disclosure.

FIG. 2 illustrates apparatus 200 for forming a graphene device such as the device of FIG. 1 according to an example embodiment.

The step of forming the graphene film 100 for example involves forming mono-layers of graphene using the apparatus 200. A similar apparatus is described in the publication entitled "Homogeneous Optical and Electronic Properties of Graphene Due to the Suppression of Multilayer Patches During CVD on Copper Foils", Z. Han et al., Adv. Funct. Mater., 2013, DOI: 10.1002/adfm.201301732, and in the US patent application published as US2014/0326700. The contents of these documents is hereby incorporated by reference to the extent permitted by the law.

The apparatus 200 comprises a reaction chamber 202 in which the graphene film is formed. For example, the reaction chamber 202 is a tube furnace or other type of chamber that can be heated.

A substrate 204, for example formed of a foil of copper or another material and having a thickness of between 0.1 and 100 µm, is placed within the chamber 202. The substrate 204 provides a surface suitable for graphene formation. In particular, the material of the substrate 204 is for example selected as one that provides a catalyst for graphene formation, and for example has relatively low carbon solubility. For example, other possible materials for forming the substrate 204 include other metals such as nickel, cobalt, or ruthenium or copper alloys such as alloys of copper and nickel, copper and cobalt, copper and ruthenium, or dielectric materials, such as zirconium dioxide, hafnium oxide, boron nitride and aluminum oxide. In some embodiments, rather than being a foil, the substrate 204 could have a 3D form having at least one of its dimensions in the range 0.1 µm to tens or hundreds of µm. Such a 3D substrate could be formed of a material suitable for graphene formation, or it could be formed of another material and have a coating, of a material suitable for graphene growth, over at least part of its surface. Furthermore, the substrate 204 could be formed on a planar or 3D surface of a further substrate, for example of copper or another material such as sapphire.

An inlet 206 of the reaction chamber 202 allows gases to be introduced into the chamber, and an outlet 208 allows gases to be extracted from the chamber. The inlet 206 is for example supplied with gas by three gas reservoirs 210A, 210B and 210C, which in the example of FIG. 2 respectively store hydrogen ($H_2$), argon (Ar), and methane ($CH_4$). In alternative embodiments discussed in more detail below, different gases could be used. In particular, rather than hydrogen, a different etching gas, in other words one that is reactive with carbon, could be used, such as oxygen. Rather than argon, another inert gas could be used, such as helium. This gas is for example used to control the overall pressure in the reaction chamber 202, and could be omitted entirely in some embodiments. Rather than methane, a different organic compound gas could be used, such as butane, ethylene or acetylene.

The inlet 206 is coupled to: reservoir 210A via a tube 212A comprising a valve 214A; reservoir 210B via a tube 212B comprising a valve 214B; and reservoir 210C via a tube 212C comprising a valve 214C. The valves 214A to 214C control the flow rates of the respective gases into the chamber.

The valves 214A to 214C are for example electronically controlled by a computing device 216. The computing device 216 for example comprises a processing device 218, under the control of an instruction memory 220 storing program code for controlling at least part of the graphene formation process.

The outlet 208 is for example coupled via a tube 222 to an evacuation pump 224 for evacuating gases from the reaction chamber 202. The rate of evacuation by the pump 224 is for example also controlled by the computing device 216. As represented by an arrow 226, the computing device may also control one or more heating elements of the reaction chamber 202 to heat the interior of the chamber during the graphene formation process.

A method of forming a graphene film using the apparatus described above is for example discussed in more detail in the US patent application published as US2014/0326700, the contents of which are hereby incorporated by reference.

Furthermore, a deposition chamber 228 is for example provided for depositing the polymer layer over the graphene film. In the embodiment of FIG. 2, a trapdoor 230 in one wall of the chamber 202 and a passageway 231 between the chambers 202, 228 permits the substrate 204 with graphene film to be transferred between the chambers 202 and 228 without being exposed to the atmosphere. In alternative embodiments, the deposition chambers 202 and 228 could be separate from each other, and the substrate 204 with graphene film could be transferred without using a passageway.

The deposition chamber 228 for example comprises an inlet 233 coupled via a further valve 214D to a supply chamber 234 for providing a precursor for depositing the polymer material to cover the graphene film. The valve is for example controlled by the coupling device 216. As mentioned above, the polymer material is for example deposited using gas phase deposition. The term "gas phase deposition" is considered here to include physical vapor deposition (PVD), chemical vapor deposition (CVD and atomic layer deposition (ALD). The precursor is for example heated in the supply chamber 234 to between 100° C. and 500° C. before being introduced as a vapor phase into the chamber 228 via the valve 214D.

Figure 3A:
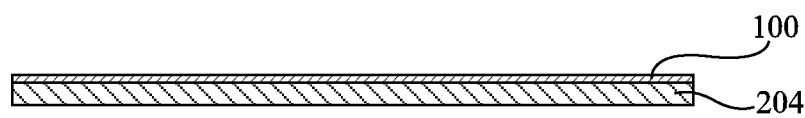
FIGS. 3A to 3C are cross-section views of the formation of a graphene device according to an embodiment of the present disclosure.
Figure 3B:
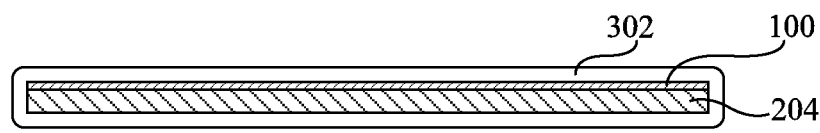
Figure 3C:
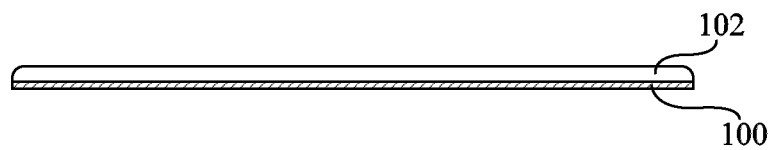

FIGS. 3A to 3C are cross-section views of a graphene device during its fabrication, for example using the apparatus of FIG. 2.

As shown in the FIG. 3A, initially it is assumed that a graphene film 100 has been formed by CVD over a substrate 204, which is for example a copper foil.

FIG. 3B illustrates an operation in which the polymer support is deposited covering the graphene film 100. In the example of FIG. 3B, the graphene is deposited over a relatively flat substrate 204, and the polymer material is deposited as a conformal layer 302 of substantially uniform thickness that encapsulates the device, including the substrate 204. For example, the device is turned over during the deposition process such that the polymer material is coated on all sides of the device. In alternative embodiments, the polymer material could be deposited only over the graphene film 100. Furthermore, rather than being deposited in the form of a layer, the polymer material could be deposited in other forms, as will be described in more detail below.

FIG. 3C illustrates a subsequent operation in which the substrate 204 is removed, for example by an etching step or by delaminating the graphene film 100 from the substrate 204. For example, the etching step involves removing the polymer coating covering the substrate 204, for example using a plasma etch, or by scraping with a sharp blade, in order to expose the surface of the substrate. The substrate is then removed, for example using a suitable etch, such as an acid etch or using an electrolysis technique.

This leaves the graphene film 100 with the polymer support 102. The present inventors have found that the polymer support 102 advantageously reduces degradation of the graphene film 100 during the separation of the graphene film 100 from the substrate 204.

An advantage of the process described herein is that no transfer operation is required, reducing the risk that the properties of the graphene film will be degraded.

Indeed, graphene is generally formed using a chemical vapor deposition (CVD) process, wherein graphene is deposited over a base substrate such as a copper foil. However, a difficulty is that it is relatively difficult to remove the graphene layer from the base substrate without damaging or polluting the graphene layer and/or degrading its conductivity.

By depositing a polymer material by gas phase deposition in contact with the graphene film, the polymer can remain attached to the graphene while the substrate is removed, for example by etching or by a delamination process, without a transfer step.

The process for forming a graphene device as described in relation to FIGS. 3A to 3C may be adapted to form a number of particular graphene-based medical devices as will now be described with reference to FIGS. 4 to 6.

Figure 4A:
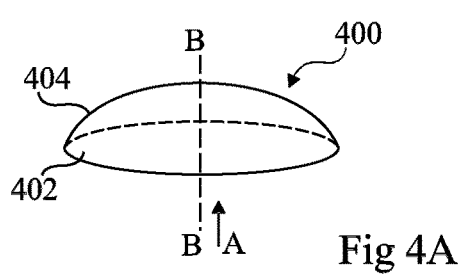
FIG. 4A illustrates an ophthalmic element comprising graphene according to an example embodiment of the present disclosure.

FIG. 4A illustrates an ophthalmic element 400 comprising graphene that is adapted to be placed on the surface of the eye. The element 400 is for example in the form of a curved plate, the outer edge of which is circular in the example of FIGS. 4A to 4D, but could have a different shape. The element 400 for example has a concave underside 402 for contacting the surface of the eye, and a convex outer surface 404, having a form that permits an eyelid to close over the element 400. The element 400 for example has a diameter of between 8 and 20 mm.

Figure 4B:
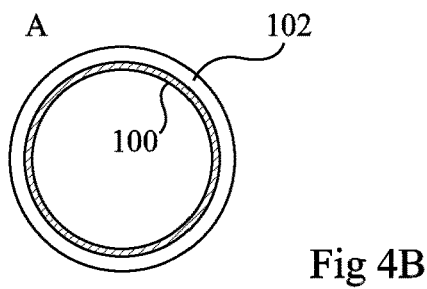
FIG. 4B is an underside view of the ophthalmic element of FIG. 4A according to an example embodiment.

FIG. 4B is an underside view of the element 400 in a direction represented by an arrow A in FIG. 4 looking towards the concave side of the element. As illustrated, the element for example comprises a graphene film 100 and a polymer support layer 102. The graphene film 100 is for example exposed on the inside surface of the element 400, such that it can make electrical contact with the surface of an eye. The polymer layer 102 provides a support for the graphene film 100, and is formed in contact with the graphene film 100 and exposed on the outer surface of the element 400. The polymer material used for the support 102 is for example parylene, in view of the biocompatible nature of this polymer.

Figure 4C:
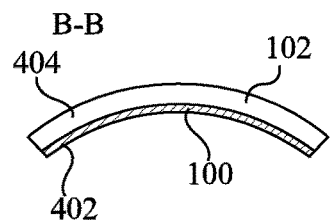
FIG. 4C is a cross-section view of the ophthalmic element of FIG. 4A according to an example embodiment.

FIG. 4C illustrates a cross-section B-B through the element of FIG. 4A, and as illustrated, the graphene film 100 and polymer support 102 together form a curved multi-layer.

Figure 4D:
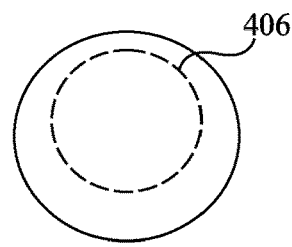
FIG. 4D illustrates a processing step for forming the ophthalmic element of FIG. 4A according to an example embodiment.

FIG. 4D represents a method step during the fabrication of the ophthalmic element 400 according to an example embodiment. The element is for example formed using a substantially spherical substrate, for example formed of a ball of copper, having at least approximately the dimensions of a human eye. The graphene film 100 is then for example formed by CVD on this substrate, and a polymer layer 102 is deposited by gas phase deposition over the graphene film 100. As represented by a dashed circle 406, a portion of the graphene/polymer multi-layer is then for example cut from the sphere in the shape of the ophthalmic element 400 and separated from the substrate, for example by a delamination process as described above, or by etching the copper forming the substrate. Alternatively, an electrochemical delamination process may be performed as described in more detail in the publication entitled "Electrochemical delamination of CVD-Grown Graphene Film: Toward the Recyclable Use of Copper Catalyst", Yu Wang et al., the contents of which is hereby incorporated by reference to the extent permitted by the law.

While an example is illustrated in FIGS. 4A to 4D in which the graphene film 100 is continuous across the ophthalmic element, the graphene film 100 could be patterned. For example, the mold used to form the ophthalmic element could comprise two different materials, one of the materials supporting graphene growth and the other material not supporting graphene growth. The patterning of these two materials across the surface of the mold on which the graphene is to be formed is selected based on the desired graphene pattern. An example of a material not supporting graphene growth is aluminum oxide. As an alternative example, a graphene etching step could be used to pattern the graphene film.

The ophthalmic element 400 may have a variety of applications, including acting as an electrode on the surface of the eye. For example, the ophthalmic element 400 could form the eye-mountable device described in the patent publication US2014/010744, in which layers of ITO (indium tin oxide) are replaced by the graphene film described herein. Alternatively, other applications of the ophthalmic element 400 include an ophthalmic shielding device, for example for shielding the eye from electromagnetic radiation such as microwaves.

Figure 5A:
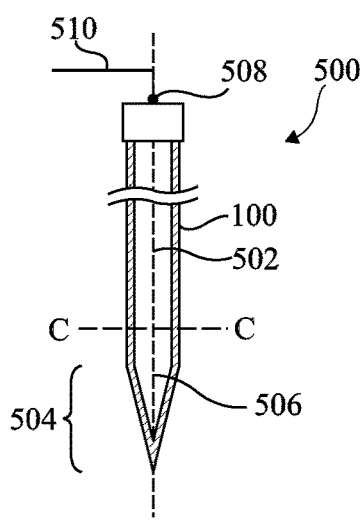
FIGS. 5A and 5B are a cross-section views of a medical implant comprising graphene according to an example embodiment of the present disclosure.

FIG. 5A is a cross-section view of a medical implant 500 comprising graphene. The element 500 is for example adapted to be inserted into human or animal tissue to act as an electrode. For example, in some applications the implant is used to monitor or stimulate neural activity. The implant is for example similar to the one disclosed in the US patent publication US2013/0090542, the contents of which is hereby incorporated by reference to the extent permitted by the law. However, whereas this document described an electrically conductive core material with an electrically non-conductive biocompatible polymer coating, the implant of FIG. 5A comprises a polymer core having an electrically conductive coating formed by a graphene film.

Indeed, as illustrated in FIG. 5A, the implant 500 for example comprises a polymer core 502 in the form of a needle, for example of parylene or polyimide, covered by a graphene film 100. The element 500 has a pointed end 504, which in the example of FIG. 5D has its point aligned with an axis 506 of the shaft of the needle, although in alternative embodiments the point coupled be offset with respect to this axis. The implant for example has a length of between a few millimeters and up to several tens of centimeters, depending on the application.

In some embodiments, some portions of the outer surface of the implant 500 could be formed of material other than graphene. For example, the point of the implant 500 could be formed of silicon or another material.

The implant comprises, for example at an opposite end to the point 504, an electrode 508, which contacts the graphene film 100. The electrode 508 for example electrically couples the graphene film 100 to a wire 510, allowing electrical signals to be applied to the implant and/or electrical signals from the implant to be detected.

Figure 5B:
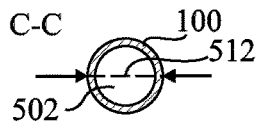

FIG. 5B is a cross-section view taken along a line C-C of FIG. 5A traversing a shaft of the implant between the pointed end 504 and the electrode 508. As shown, the implant is for example substantially circular in cross-section, although in alternative embodiment other shapes would be possible. A diameter of the implant is for example in the range 20 μm to 500 μm.

Figure 5C:
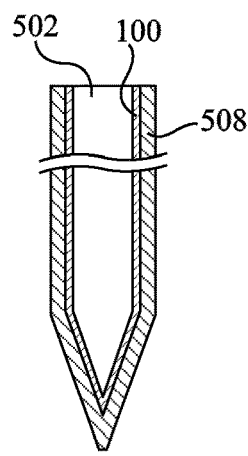
FIGS. 5C and 5D are cross-section views showing steps in a method of forming the implant of FIGS. 5A and 5B according to an example embodiment.
Figure 5D:
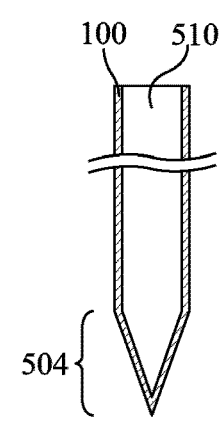

FIGS. 5C and 5D are cross-section views illustrating examples of process steps for forming the implant 500 of FIG. 5A.

As shown in FIG. 5C, the implant of FIG. 5A is for example formed using a mold 508, for example formed of copper, and having an inside surface having the desired outer form of the implant 500. The graphene film 100 is then for example formed by CVD on the inside surface of the mold, for example using the chamber 202 of the apparatus of FIG. 2. A gas phase deposition of the polymer support 502 is then performed to fill the mold 508, and contact the graphene film 100.

As shown in FIG. 5D, the mold 508 is then removed, for example using an etching step, leaving the shaft and pointed end 504 of the implant 500. The electrode 508 (not shown in FIG. 5D) is for example in the form of a cap placed over the end of the implant, opposite to the pointed end 504. Alternatively, the electrode 508 could be formed by a portion of the mold that is for example protected so that it is not etched when the rest of the mold is removed, and which thus remains in contact with the graphene film 100.

Figure 6A:
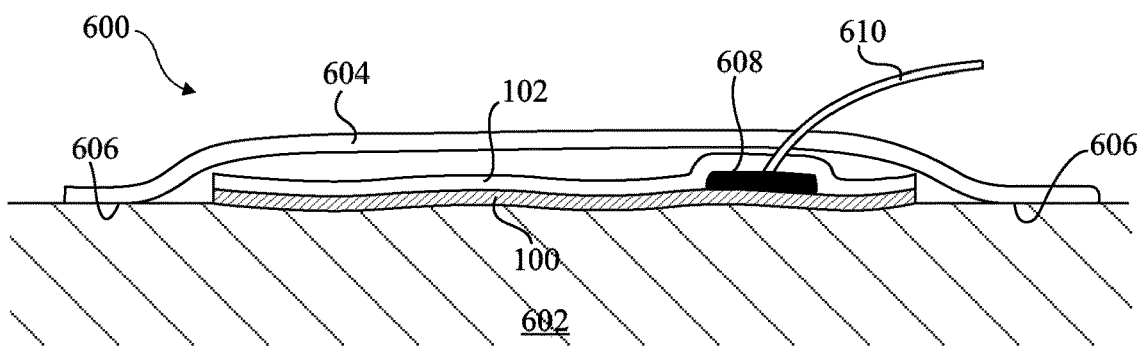
FIG. 6A is a cross-section view of a medical patch comprising a graphene film according to a further embodiment of the present disclosure.

FIG. 6A is a cross-section view of a conductive patch 600 comprising a graphene film 100. FIG. 6A illustrates an example in which the patch is employed contacting the surface of a portion of skin 602 of a human or animal body. The graphene film 100 of the patch is for example positioned to be exposed to and make contact directly with the surface of the skin 602, and it has a support 102 of polymer material in the form of a layer formed over it. The polymer layer 102 is for example of parylene. A further band 604 of polymer for example covers the graphene and polymer multi-layer 100, 102, and holds it in place against the skin. For this, the band 604 for example extends beyond the multi-layer 100, 102 on each side to make direct contact with the surface of the skin 602. It also for example has an adhesive layer 606 over at least a portion of its surface that contacts with the skin 602.

An electrode 608 for example contacts the graphene film. The polymer layer 102 for example has a thickness of between 10 nm and 5 mm, and an opening is formed in a portion of the polymer layer 102 in order to expose the surface of the graphene film. The electrode 608 is then for example formed on the graphene film, and in some embodiments, a further polymer deposition is performed to cover the electrode 608. An antenna 610 for example couples the electrode 608 to a monitoring device, passing through the band 604.

The patch 600 of FIG. 6A is only represented in cross-section, and it will be clear to those skilled on the art that in plan view the graphene/polymer multi-layer 100, 102, and the band 604, could have any form, for example rectangular or circular. The graphene film 100 for example has a surface area of between 5 and 50 mm$^2$ that contacts the skin 602.

An advantage of the embodiment of FIG. 6A is that the graphene/polymer multi-layer 100, 102 is relatively supple, enabling it to follow contours in the surface of the skin, including wrinkles, while maintaining relatively high conductivity with the skin 602.

In the example of FIG. 6A, the electrode 608 contacts a relatively small zone of the graphene film 100. However, in order to improve electrical contact with all parts of the graphene film 100, in alternative embodiments the electrode 608 is substantially annular, making contact in a perimeter zone of the graphene film 100, as will now be described with reference to FIG. 6B.

Figures 6B, 7C:
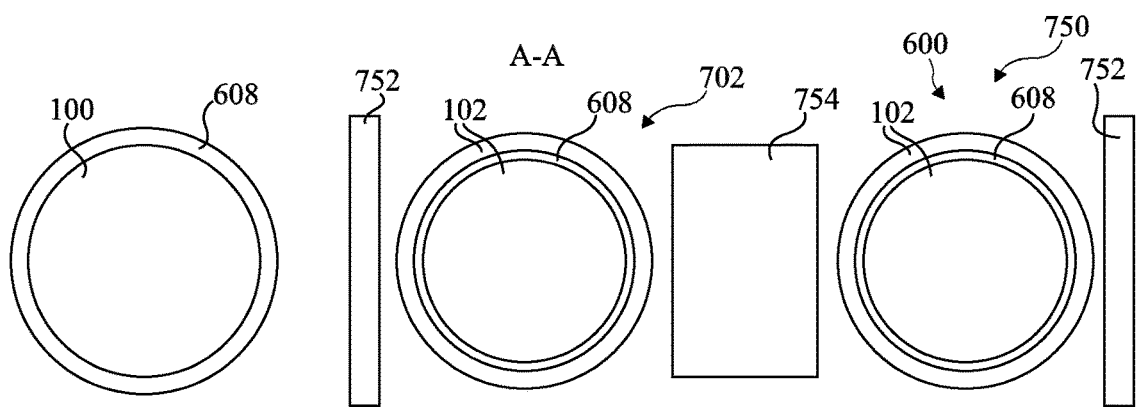
FIG. 6B is a plan view of a graphene film and contact electrode according to an example embodiment of the present disclosure.
FIG. 7C illustrates a view of the medical patch of FIG. 7B taken in a plane A-A of FIG. 7B.

FIG. 6B is a plan view of the graphene film 100, and also illustrates an annular electrode 608 used for making electrical contact with the graphene film 100. In particular, the electrode 608 for example surrounds the zone in which the graphene film 100 makes contact with the wound. For example, the electrode 608 is formed of a material such as a resin or glue mixed with carbon to render it conductive. While an example is illustrated in which the electrode 608 is annular, other forms would be possible, such as rectangular.

In some applications, the patch 600 could be used for administering a medicine and/or for the treatment of open wounds, as will now be described in more detail with reference to FIGS. 7A, 7B and 8.

Figure 7A:
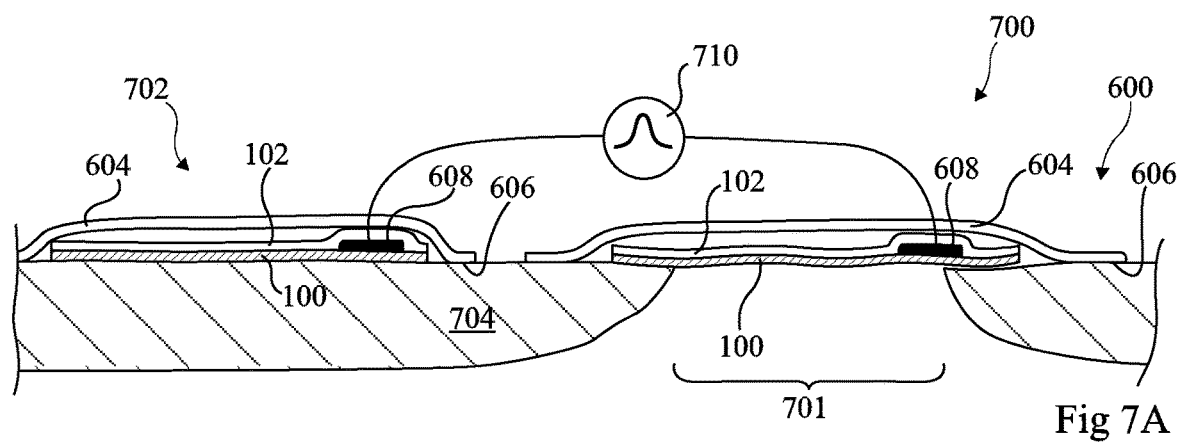
FIG. 7A is a cross-section view of a wound treatment apparatus comprising the medical patch of FIG. 6A according to an example embodiment.

FIG. 7A illustrates an apparatus 700 for treating wounds and/or administering medicine using the medical patch 600 of FIG. 6A. As illustrated, the patch 600 is for example applied as a wound dressing covering an open wound 701. Alternatively, the patch 600 could be applied to skin in a similar fashion to the example of FIG. 6A, and used for drug delivery. A further patch 702, which is for example very similar to the patch 600, is for example applied to the patient's skin in the vicinity of the wound, for example within a distance of 20 cm or so from the wound. The features of the patch 702 have been labelled with like reference numerals to the patch 600, and will not be described again in detail. In alternative embodiments, a different type of conductive patch could be used to implement the further patch 702.

The electrodes 608 of each of the patches 600, 702 are for example coupled to a voltage application module 710. The module 710 is for example adapted to apply voltage pulses across the electrodes 608 of the patches 600, 702 in order to drive a current through the patient's tissue in the vicinity of the wound 701 or the patient's skin.

Medicine is for example delivered through the skin by the patch 600 using a process of iontophoresis. In such a case, the medicine is for example in the form of a cream or gel positioned between the graphene film 100 and the skin. A DC current of between 0.1 and 5 mA is for example applied between the electrodes of the patches 600, 700. For example, thus us achieved by applying a voltage in the range 5 to 40 V. This for example generates a current density in the skin of between 0.01 and 0.1 mA/cm$^2$. In some embodiments, a pulsed signal rather than a DC signal could be applied.

For wound treatment, a process of electrical stimulation is for example performed, as described in more detail in the publication by L. C. Kloth entitled "Electrical Stimulation Technologies for Wound Healing", Adv Wound Care, Feb. 1, 2014, 3(2): 81-90, the contents of which is hereby incorporated by reference. For such a treatment, there are various possible voltage levels and frequencies that could be employed. In some embodiments, a DC signal could be applied, for example having a voltage in the range of 5 to 60 V. Alternatively, a monophasic or diphasic pulsed current could be applied, having a frequency of anywhere between 1 and 100 kHz, and a voltage for example in the range 50 to 500 V.

Figure 7B:
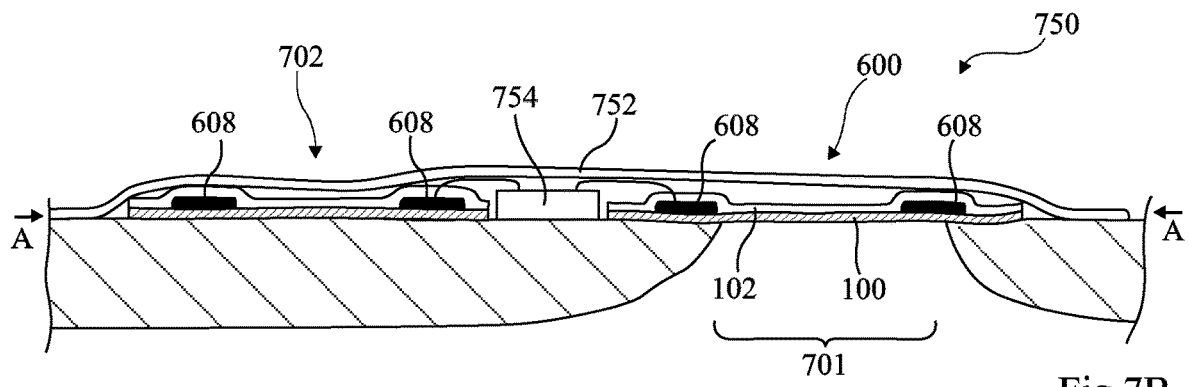
FIG. 7B is a cross-section view of a medical patch having a wound dressing and contact electrode according to an example embodiment.

FIG. 7B illustrates a medical patch 750 for treating wounds and/or administering medicine similar to that of FIG. 7A, but in which both the wound dressing portion 600 and the electrode patch 702 use the annular electrode 608 of FIG. 6B.

FIG. 7C illustrates a view of the medical patch 750 taken in a plane A-A shown in FIG. 7B passing through the annular electrodes 608 of the wound dressing 600 and of the electrode patch 702.

The medical patch 750 of FIGS. 7B and 7C comprises both the wound dressing portion 600 covering a wound 701, and the electrode patch 702 contacting the patient's skin, under a same adhesive band 752 that holds the wound dressing 600 and electrode patch 702 in electrical contact with the patient. Furthermore, in the example of FIGS. 7B and 7C there is no wire leaving the patch 750, and instead the patch 750 comprises a circuit 754 coupled by wires to the annular electrodes 608 of the wound dressing 600 and electrode patch 702. The circuit 754 for example comprises a power source, such as a battery, for driving a current between the graphene films 100 of the wound dressing 600 and electrode patch 702. In other embodiments, in addition to or instead of using a battery, the circuit 754 may comprise a coil antenna and a capacitor fed with charge generated by the coil antenna. In this way, the wound dressing can be powered wirelessly using a non-contact inductive coupling. For example, such a wireless non-contact inductive coupling is described in more detail in the US patent application published as US20140336597, the contents of which are hereby incorporated by reference to the extent permitted by the law.

Figure 8:
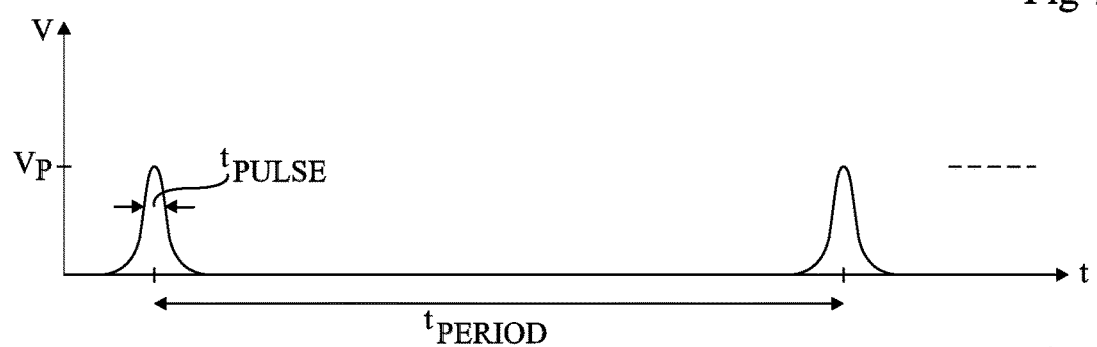
FIG. 8 is a timing diagram illustrating a voltage signal applied by the apparatus of FIG. 7A according to an example embodiment.

FIG. 8 illustrates an example of the voltage signal applied to across the electrodes 608 of the patches 600, 702 to provide electrical stimulation for wound healing. For example, the voltage pulses have a peak voltage amplitude $V_P$ of around 100 V. Each pulse for example has a duration $t_{PULSE}$, and the no-current interval between successive pulses represents up to 99% or more of each period $t_{PERIOD}$, such that the total current per second delivered to tissue does not exceed more than 1.2-1.5 mA. Thus for a voltage $V_P$ of 100 V, the paired pulse charge is for example only around 3-3.5 µC, and for a pulse rate of 100 pulses/s, the total charge accumulation (dosage) does not for example exceed 350 µC/s.

Such a treatment is for example applied for a period of between 5 and 60 minutes, and repeated on a daily basis until the wound has healed.

In some embodiments, the apparatus 700 of FIG. 7A or medical patch 750 of FIG. 7B further comprises means for detecting the resistance of the wound between the graphene film 100 of the wound dressing 600 and the graphene film 100 of the electrode patch 702. For example, the voltage application module 710 of FIG. 7A and/or the circuit 754 of FIG. 7B comprises a current sensor and/or voltage sensor for detecting the current and/or voltage applied between the wound dressing 600 and the electrode patch 702, enabling the resistance to be determined. For example, the measured resistance may provide an indication of the state of the wound, a high resistance indicating that the wound is becoming dry and/or is healing.

In some embodiments the graphene film 100 of the wound dressing 600 could also be patterned to form a plurality of pixels such that the resistance information of the pixels can provide an image of the wound. For example, the graphene film could be pattered as shown in FIG. 7 of the U.S. Pat. No. 7,945,302, and the teaching described in this document could be applied to the medical patch described herein to provide such an image. The contents of U.S. Pat. No. 7,945,302 is hereby incorporated by reference to the extent permitted by the law.

Advantageously, at least part of the graphene film 100 of the patch 600 remains in place on the tissue of the patient when the patch is removed, as will now be described with reference to FIG. 9.

Figure 9:
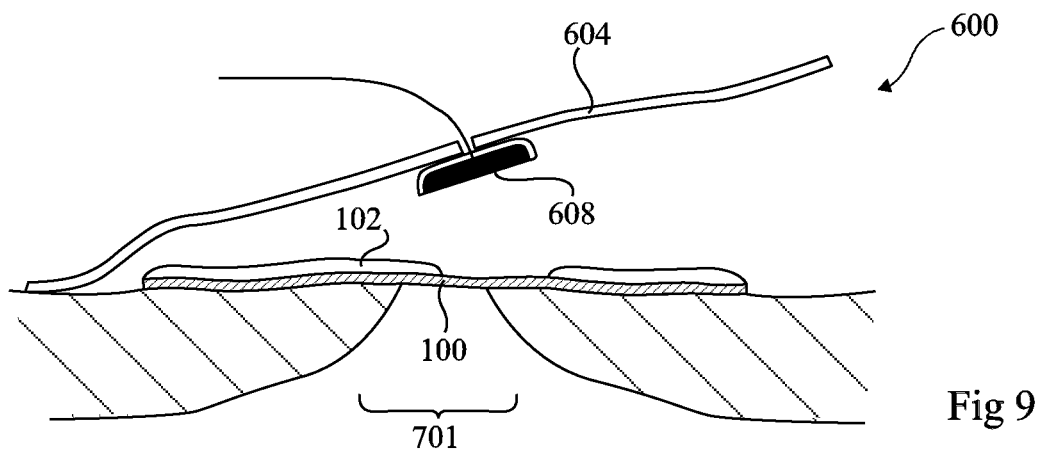
FIG. 9 illustrates removal of the patch of FIGS. 6 and 7 according to an example embodiment.

FIG. 9 illustrates the patch 600 in the process of being removed, for example after the wound 701 has started to heal and has thus reduced in size. The band 604 and the electrode 608 of the patch 600 for example separate from the multi-layer of graphene 100 and polymer 102, which remain covering the wound 701. For example, an adhesive is present between the protrusion formed by the electrode 608 and the band 604, such that the electrode is pulled away as the band 604 is removed from the skin. However, there is for example no adhesive, or a relatively weak adhesive, present between the graphene/polymer multi-layer and the band 604. Advantageously, graphene is a material that will be progressively absorbed by tissue. Furthermore, a polymer layer that is relatively thin, for example formed of parylene of between 10 and 20 nm in thickness, can also be absorbed.

Alternatively, the graphene layer 100 may be a multi-layer, and the polymer layer 102 may be glued or otherwise fixed to the band 604, such that the patch delaminates within the graphene layer 100. Thus only one or a few graphene layers for example remain covering the wound when the patch 600 is removed.

The advantage of leaving at least part of the graphene/polymer multi-layer covering the wound when the patch 600 is removed is that this reduces damage to wound caused by the removal process, and further reduces the chance of infection by leaving a barrier in place. Furthermore, it has been found that a graphene film can be absorbed by a body, meaning that the graphene film will be broken down and disappear without further intervention.

In some embodiments, only all or part of the graphene film 100 remains covering the wound, and the polymer film 102 remains attached to the band 604 when the wound dressing is removed. For example, the graphene film is formed of multiple layers of graphene, such that at least one layer of graphene remains attached to the polymer layer when the dressing is removed, and at least one layer of graphene remains covering the wound. In yet further embodiments, the polymer film 102 is formed of a material that can be absorbed by the body like the graphene film, so that even when the polymer layer remains covering the wound, it is broken down and removed naturally by the body. An example of such a polymer material that could be used to form the polymer layer 102 is hyaluronic acid.

A further advantage of the use of a graphene and polymer structure for wound dressing is that the patch can be highly transparent. This is not only good for the aesthetics of the dressing, but also for example permits natural light to reach the wound, aiding the healing process. Furthermore, the transparency of the dressing permits the state of the wound during the healing process to be monitored visually and/or using specialized equipment. Indeed, graphene is grey in color and thus does not modify the color of the underlying wound, allowing this to be monitored visually. Furthermore, an analysis based on the Doppler Effect can be performed, known as LDF (Laser Doppler Flowmetry) as will now be described with reference to FIG. 10.

Figure 10:
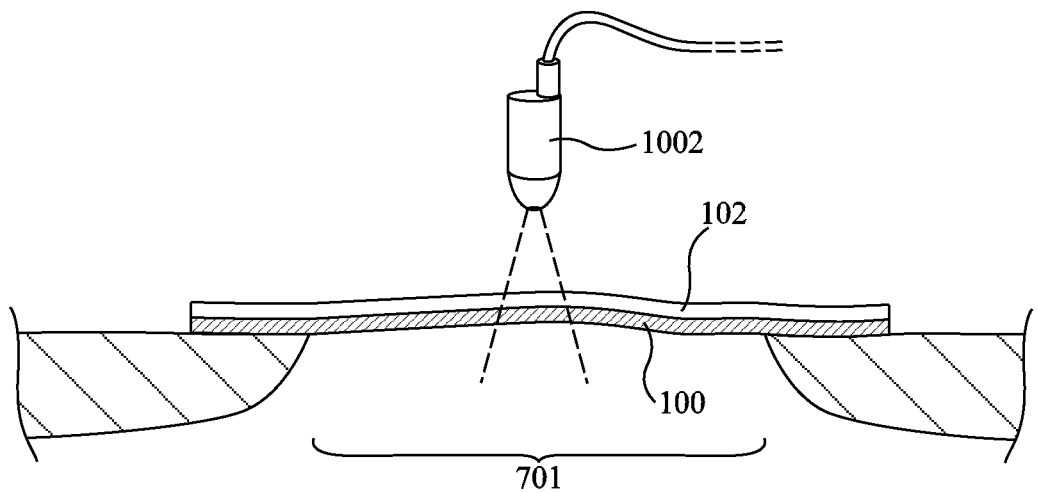
FIG. 10 is a cross-section view of a transparent wound dressing according to an example embodiment.

FIG. 10 illustrates a wound 701 covered by a graphene/polymer patch 100, 102. A hand-held continuous wave Doppler laser equipment 1002 is used to take measurements of the wound for assessment. For example, the equipment 1002 is used for laser Doppler imaging as described in more detail in the publication by Stan Monstrey et al. entitled "Assessment of burn depth and burn wound healing potential", BURNS 34 (2008) 761-769, and/or in the publication by G. C. Zografos et al. entitled "Laser Doppler Flowmetry in Evaluation of Cutaneous Wound Blood Flow Using Various Suturing Techniques", LASER DOPPLER FLOWMETRY, Vol. 215, No. 3, Ann. Surg. March 1992, the contents of these publications being incorporated herein by reference to the extent permitted by the law. For example, analysis may be based on a detection of the speed of red blood cells in the wound, where movement of the red blood cells above a certain speed indicates a healthy healing process, and slow moving or stationary red blood cells indicates an unhealthy wound.

While FIG. 10 illustrates a case in which the adhesive band 604 is removed prior to performing LDF, in alternative embodiments, the adhesive band 604 could be transparent, permitting LDF to be performed without removing the adhesive band 604.

Figure 11:
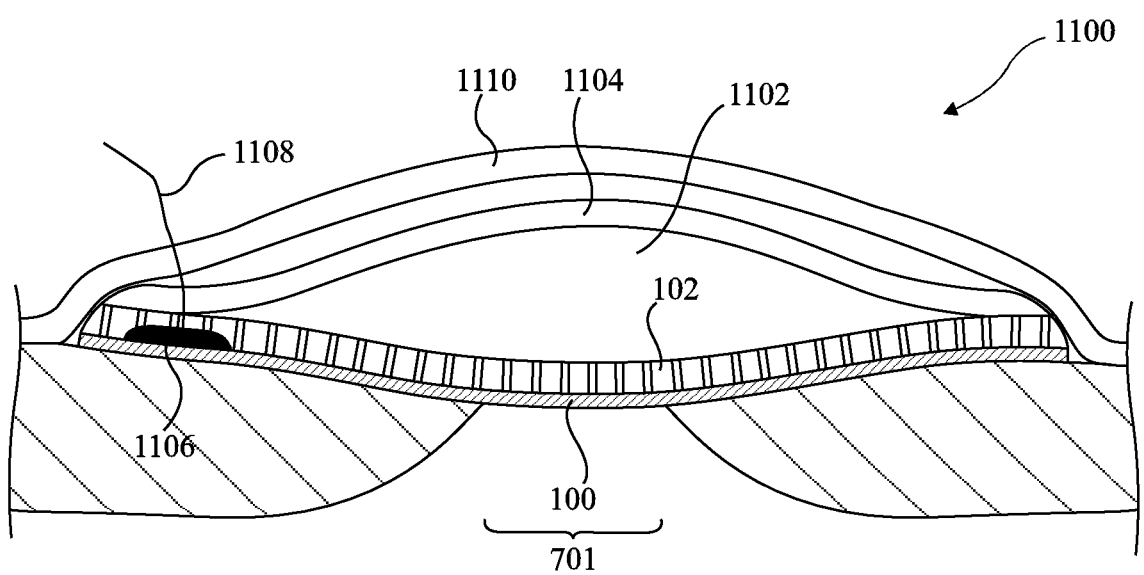
FIG. 11 is a cross-section view of a hydrocolloidal dressing according to an example embodiment.

FIG. 11 is a cross-section view of a conductive patch 1100 comprising a graphene film 100. FIG. 11 illustrates an example in which the patch provides a hydrocolloidal blister dressing. This dressing for example comprises a porous polymer layer 102. For example, the polymer material could be hyaluronic acid, which is inherently porous, or the polymer material could be parylene or another non-porous polymer which is rendered porous by creating channels through the layer for example using a lithography step, thereby providing a micro-structure. The channels through the porous polymer layer 102 permit oxygen and water to flow between the wound and a pad 1102 formed of a hydrocolloid. The pad 1102 is for example held by a layer 1104 of a non-porous polymer material. The hydrocolloid acts as a sponge, absorbing the exudate from the wound, and providing moisture to the wound if it becomes dry. The graphene film 100 contacts the wound or blister, and is electrically coupled, for example via a contact 1106, with a wire 1108. An adhesive band 1110 is for example provided for holding the hydrocolloidal dressing in contact with the wound.

In operation, the graphene film 100 can receive an electrical current as described in relation to FIGS. 7A and 7B using a further electrode patch (not illustrated in FIG. 11).

Furthermore, Laser Doppler Flowmetry (LDF) as described above in relation to FIG. 10 could also be performed in the embodiment of FIG. 11, the pad 1102 and some or all of the layers 100, 102, 1104 and 1110 for example being transparent such that LDF can be performed through them.

An advantage of the medical devices described herein is that they have a good electrical conductively due to the graphene film, and are capable of maintaining close electrical contact with the skin or tissue of the human or animal due to the use of the polymer material supporting the graphene film which adapts to contours in the surface of the body against which the device is applied.

Furthermore, by using a graphene formation process in which a polymer layer is deposited over the graphene film using gas phase deposition, the electrical conducting properties and mechanical properties of the graphene film can be particularly well conserved as the mold is removed. Indeed, gas phase deposition allows a thin polymer coating of relatively uniform thickness to be applied that has high conformity with the roughness of the surface of the graphene film, by closely following the contours of the graphene film. In view of its high conformity and uniformity, such a polymer layer exerts a lower stress on the graphene layer than would be possible with other deposition techniques such as spin coating.

Furthermore, gas phase deposition allows a supporting polymer layer to be realized that strictly conforms to a 3-dimensional shape of the graphene film, both at the nanoscale and at the microscale, respectively helping to preserve the integrity of the film by matching the wrinkles and thereby providing good electrical conductivity and helping to maintain the global 3D shape of the graphene film after the mold removal, allowing depositions on complex shapes such as implants, etc.

Having thus described at least one illustrative embodiment, various alterations, modifications and improvements will readily occur to those skilled in the art.

For example, it will be apparent to those skilled in the art that while various devices comprising graphene have been described above and represented in the figures, there are many alternative applications of the method of forming the graphene and polymer multi-layer as described herein.

Furthermore, the various features described in relation to the various embodiments could be combined, in alternative embodiments, in any combination. For example, the use of hyaluronic acid to form the polymer layer and provide a therapeutic action may be combined with the use of a pad of a hydrocolloid positioned close to the wound to absorb exudate from the wound.

Such alterations, modifications, and improvements are intended to be within the scope of the invention. Accordingly, the foregoing description is by way of example only and is not intended as limiting. The invention is limited only as defined in the following claims and the equivalents thereto.

The invention claimed is:

1. A method of forming a medical device, the method comprising:
    forming a graphene film over a substrate;
    depositing, by gas phase deposition, a polymer material covering a surface of the graphene film;
    removing the substrate from the graphene film, wherein the polymer material forms a support for the graphene film;
    providing an adhesive band covering the polymer support and holding the graphene film in contact with a body of an animal or human; and
    electrically coupling a wire contact to the graphene film.

2. The method of claim 1, wherein the polymer material comprises a polymer from the n-xylylene family.

3. The method of claim 2, wherein the polymer material comprises parylene.

4. The method of claim 1, wherein removing the substrate from the graphene film is performed by a process of electrochemical delamination.

5. The method of claim 1, wherein electrically coupling the wire contact to the graphene film comprises, prior to depositing the polymer material, forming the wire contact on the surface of the graphene film, wherein depositing the polymer material comprises coating the wire contact with the polymer material.

6. The method of claim 1, further comprising forming a conductive electrode patch of the conductive medical patch and a current supply circuit, the current supply circuit being adapted to apply a current between the graphene film and the conductive electrode patch, wherein the adhesive band is also suitable for holding the conductive electrode patch in contact with the body.

7. The method of claim 1, wherein the conductive medical patch is a transparent hydrocolloidal dressing, the graphene film forming an external surface for contact with a wound, and the polymer material being a porous layer positioned between the graphene film and a pad formed of a hydrocolloid.

8. The method of claim 1, wherein the polymer material is deposited over the graphene film in a layer of between 5 and 40 nm in thickness.

9. A method for forming an ophthalmic element, the method comprising:
  forming a graphene film over a substrate;
  depositing, by gas phase deposition, a polymer material covering a surface of the graphene film; and
  removing the substrate from the graphene film, wherein the polymer material forms a support for the graphene film;
  wherein the substrate on which the graphene film is formed has a curved surface having a shape compatible with the surface of an eye.

10. The method of claim 9, wherein a surface of the substrate on which the graphene film is formed comprises a pattern of first and second materials, the first material and not the second material supporting graphene formation, the method comprising selectively forming said graphene film over said first material and not over said second material.

11. A method for forming an implant, the method comprising:
  forming a graphene film over a substrate;
  depositing, by gas phase deposition, a polymer material covering a surface of the graphene film; and
  removing the substrate from the graphene film, wherein the polymer material forms a support for the graphene film;
  wherein the substrate on which the graphene film is formed is a mold having an inner surface having the form of the implant, and wherein after the graphene film has been deposited on the inner surface of the mold, the mold is filled by the polymer material to form a polymer core of the implant that supports the graphene film.

12. The method of claim 11, wherein a portion of said mold is not removed such that it remains in contact with the graphene film and forms an electrode of the implant.

* * * * *